United States Patent
Okamoto (10) Patent No.: US 11,540,708 B2
(45) Date of Patent: Jan. 3, 2023

(54) ENDOSCOPE REPROCESSING METHOD AND ENDOSCOPE REPROCESSOR

(71) Applicant: OLYMPUS CORPORATION, Tokyo (JP)

(72) Inventor: Haruhiko Okamoto, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 450 days.

(21) Appl. No.: 16/744,336

(22) Filed: Jan. 16, 2020

(65) Prior Publication Data

US 2020/0196850 A1 Jun. 25, 2020

Related U.S. Application Data

(63) Continuation of application No. PCT/JP2018/016591, filed on Apr. 24, 2018.

(30) Foreign Application Priority Data

Aug. 30, 2017 (JP) .............................. JP2017-165977

(51) Int. Cl.
*A61B 1/00* (2006.01)
*A61B 1/12* (2006.01)
*A61B 90/70* (2016.01)
*A61L 2/18* (2006.01)
*A61L 2/28* (2006.01)

(52) U.S. Cl.
CPC .......... *A61B 1/125* (2013.01); *A61B 1/00002* (2013.01); *A61B 1/00057* (2013.01); *A61B 1/00128* (2013.01); *A61B 1/123* (2013.01); *A61B 90/70* (2016.02); *A61L 2/18* (2013.01); *A61L 2/28* (2013.01); *A61B 2090/701* (2016.02); *A61L 2202/14* (2013.01); *A61L 2202/17* (2013.01); *A61L 2202/24* (2013.01)

(58) Field of Classification Search
None
See application file for complete search history.

(56) References Cited

U.S. PATENT DOCUMENTS

2007/0048183 A1 3/2007 Nguyen et al.
2012/0073614 A1 3/2012 Otani et al.

FOREIGN PATENT DOCUMENTS

| EP | 1757313 A1 | 2/2007 |
|---|---|---|
| JP | 2007-061611 A | 3/2007 |
| JP | 2012-066018 A | 4/2012 |
| JP | 2012-071030 A | 4/2012 |

OTHER PUBLICATIONS

International Search Report dated Jul. 24, 2018 issued in PCT/JP2018/016591.

*Primary Examiner* — Levon J Shahinian
(74) *Attorney, Agent, or Firm* — Scully, Scott, Murphy & Presser, P.C.

(57) ABSTRACT

An endoscope reprocessing method includes: cleaning, disinfecting, or sterilizing an inside of a pipe line and an outer surface of an endoscope accommodated in a treatment tank; rinsing the outer surface of the endoscope with a rinsing liquid while filling the inside of the pipe line of the endoscope with gas; collecting a first sample from the rinsing liquid used for rinsing the outer surface of the endoscope; rinsing the inside of the pipe line of the endoscope with the rinsing liquid; and collecting a second sample from the rinsing liquid used for rinsing the inside of the pipe line of the endoscope.

18 Claims, 7 Drawing Sheets

FIG. 8

ENDOSCOPE REPROCESSING METHOD AND ENDOSCOPE REPROCESSOR

CROSS REFERENCE TO RELATED APPLICATION

This application is a continuation application of PCT/JP2018/016591 filed on Apr. 24, 2018 and claims benefit of Japanese Application No. 2017-165977 filed in Japan on Aug. 30, 2017, the entire contents of which are incorporated herein by this reference.

BACKGROUND OF INVENTION

1. Field of the Invention

The present invention relates to an endoscope reprocessing method and an endoscope reprocessor for performing at least one of cleaning processing, disinfection processing, and sterilization processing on an endoscope.

2. Description of the Related Art

Endoscopes used in a medical field are subjected to reprocessing, such as cleaning processing and disinfection processing, after use. Further, as disclosed in, for example, Japanese Patent Application Laid-Open Publication No. 2012-66018, an endoscope cleaning/disinfecting apparatus that automatically performs reprocessing on an endoscope is known.

In addition, there is a method for detecting the presence or absence of bacteria attached to the endoscope after the reprocessing in order to evaluate whether or not the reprocessing has been appropriately performed on the endoscope. For example, in the endoscope cleaning/disinfecting apparatus disclosed in Japanese Patent Application Laid-Open Publication No. 2012-66018, in order to detect the presence or absence of bacteria attached to the endoscope after the reprocessing, a configuration in which a rinsing liquid used for processing of rinsing the endoscope passes through a filter that captures bacteria is provided. In the technology disclosed in Japanese Patent Application Laid-Open Publication No. 2012-66018, when culturing bacteria using a filter removed from the endoscope cleaning/disinfecting apparatus as a culture medium is performed and no growth of bacteria is seen, it is determined that the reprocessing has been appropriately performed on the endoscope.

SUMMARY OF THE INVENTION

According to one aspect of the present invention, there is provided an endoscope reprocessing method including: cleaning, disinfecting, or sterilizing an inside of a pipe line and an outer surface of an endoscope accommodated in a treatment tank; rinsing the outer surface of the endoscope with a rinsing liquid while filling the inside of the pipe line of the endoscope with gas; collecting a first sample from the rinsing liquid used for rinsing the outer surface of the endoscope; rinsing the inside of the pipe line of the endoscope with the rinsing liquid; and collecting a second sample from the rinsing liquid used for rinsing the inside of the pipe line of the endoscope.

According to another aspect of the present invention, there is provided an endoscope reprocessor including: a treatment tank configured to accommodate an endoscope and to be able to store a liquid; a fluid sending mechanism configured to send a fluid into a pipe line of the endoscope accommodated in the treatment tank; a liquid introduction mechanism configured to introduce a rinsing liquid into the treatment tank; a sample collection device configured to collect a sample from the liquid in the treatment tank; and a processor, in which the processor cleans, disinfects, or sterilizes an inside of the pipe line and an outer surface of the endoscope accommodated in the treatment tank, introduces the rinsing liquid into the treatment tank by the liquid introduction mechanism and rinses the outer surface of the endoscope with the rinsing liquid while sending gas from the fluid sending mechanism and filling the inside of the pipe line of the endoscope with gas, collects a first sample from the rinsing liquid used for rinsing the outer surface of the endoscope by the sample collection device, sends the rinsing liquid from the fluid sending mechanism and rinses the inside of the pipe line of the endoscope with the rinsing liquid, and collects a second sample from the rinsing liquid used for rinsing the inside of the pipe line of the endoscope by the sample collection device.

DETAILED DESCRIPTION OF THE PREFERRED EMBODIMENT(S)

Hereinafter, preferable embodiments of the present invention will be described with reference to the drawings. Note that in the respective drawings used for the following description, the scale of each component is made different such that each component has a size that makes it possible to recognize the components in the drawing, and the present invention is not limited only to the quantity of the components, the shape of the components, the ratio of the size of the components, and the relative positional relationship of each component described in the drawings.

First Embodiment

Figure 1:
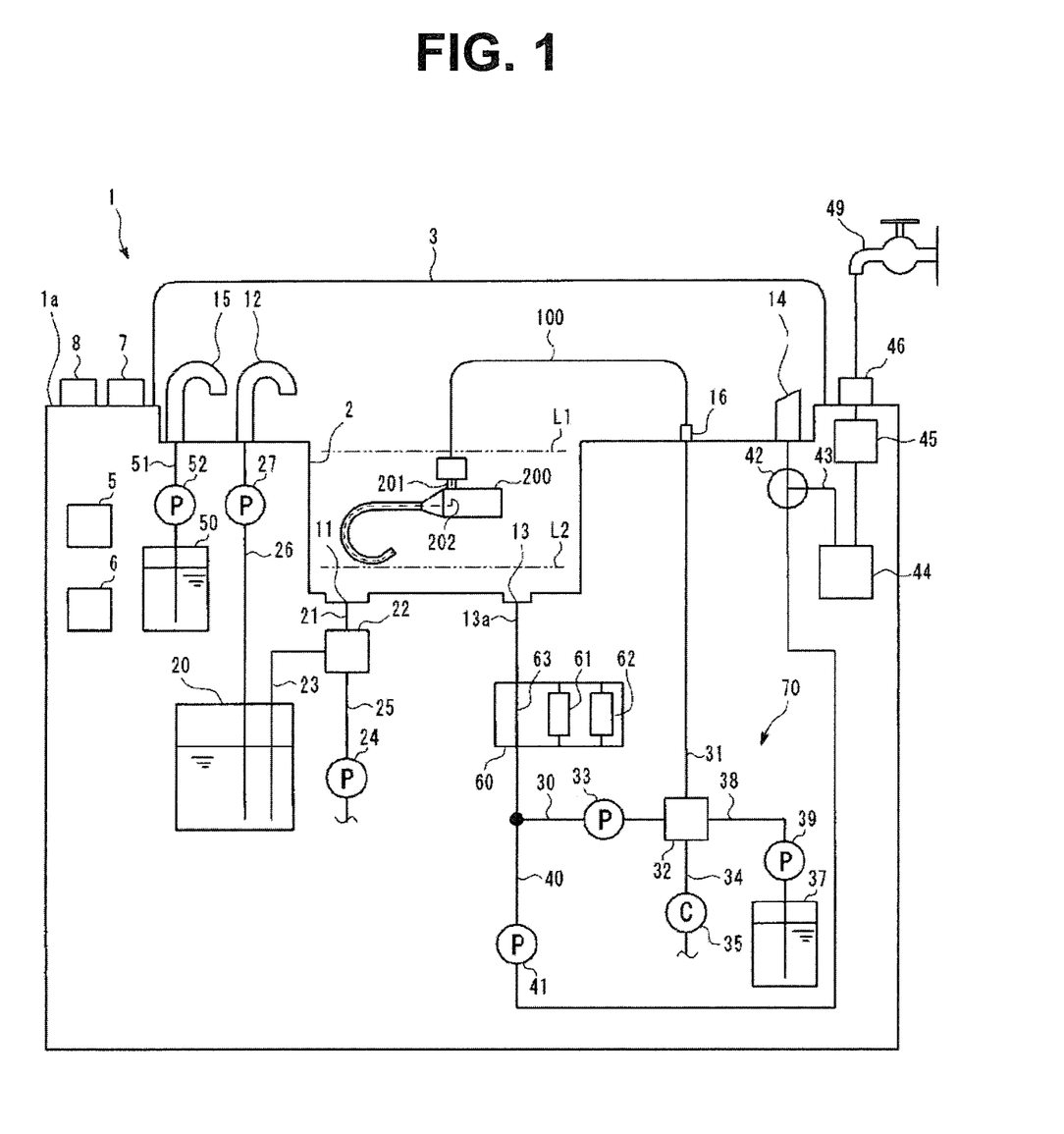
FIG. 1 is a view illustrating a configuration of an endoscope reprocessor according to a first embodiment.

Hereinafter, an example of an embodiment of the present invention will be described. An endoscope reprocessor 1 illustrated in FIG. 1 is a device that performs reprocessing on an endoscope 200. The reprocessing here is not particularly limited, and may be any of rinsing processing with water, cleaning processing for removing dirt, such as organic matter, disinfection processing for neutralizing predetermined microorganisms, sterilization processing for eliminating or killing all microorganisms, or a combination of these processes.

Note that in the following description, "upper" refers to a position that is further away from the ground relative to the comparison target, and "lower" refers to a position closer to the ground relative to the comparison target. Moreover, the height in the following description indicates the height relationship along the gravity direction.

The endoscope reprocessor 1 includes a control portion 5, a power supply portion 6, a treatment tank 2, and a sample collection device 60.

The control portion 5 can be configured as a processor having an arithmetic device (CPU), a storage device (RAM), an auxiliary storage device, an input/output device, a power control device, and the like, and has a configuration that executes a predetermined program according to an instruction from a user and controls operations of each part that configures the endoscope reprocessor 1. The operations of each configuration included in the endoscope reprocessor 1 in the following description are controlled by the control portion 5 even in a case where there is no particular description. In the processor, for example, functions of each part may be realized by individual hardware, or a part of each portion may be realized by integrated hardware. For example, the processor includes hardware, and the hardware can include at least one of a circuit that processes a digital signal and a circuit that processes an analog signal. As the processor, various processors, such as a digital signal processor (DSP), can be used other than the arithmetic unit (CPU). Further, the processor may be an application specific integrated circuit (ASIC) or a hardware circuit based on field programmable gate array (FPGA).

An operation portion 7 and a display portion 8 configure a user interface for exchanging information between the control portion 5 and the user. The operation portion 7 includes an operation member that receives an operation instruction from the user, such as a push switch or a touch sensor. Note that the operation instruction from the user is converted into an electric signal by the operation portion 7 and inputted into the control portion 5. The operation instruction from the user is, for example, an instruction to start reprocessing. The operation portion 7 may be provided in an electronic device separated from a main body portion 1a of the endoscope reprocessor 1 that performs wired communication or wireless communication with the control portion 5.

Further, the display portion 8 includes, for example, a display device that displays images or characters, a light emitting device that emits light, a speaker that emits sound, a vibrator that emits vibration, or a combination of these components. The display portion 8 outputs information from the control portion 5 to the user. The display portion 8 may be provided in an electronic device separated from the main body portion 1a of the endoscope reprocessor 1 that performs wired communication or wireless communication with the control portion 5.

The power supply portion 6 supplies electric power to each part of the endoscope reprocessor 1. The power supply portion 6 distributes electric power obtained from the outside, such as a commercial power supply, to each part. Note that the power supply portion 6 may include a power generation device or a battery.

The treatment tank 2 has a recessed shape having an opening portion and can store a liquid in the treatment tank 2. The endoscope 200 can be disposed in the treatment tank 2. In the treatment tank 2, a plurality of endoscopes 200 may be arranged.

On the upper part of the treatment tank 2, a lid 3 for opening and closing the opening portion of the treatment tank 2 is provided. In a case where the reprocessing is performed on the endoscope 200 in the treatment tank 2, the opening portion of the treatment tank 2 is closed by the lid 3.

The treatment tank 2 is provided with a cleaning liquid nozzle 15, a medicinal solution nozzle 12, a drainage port 11, a circulation port 13, a circulation nozzle 14, and an endoscope pipe line connection portion 16.

The cleaning liquid nozzle 15 is an opening portion that communicates with a cleaning liquid tank 50 that stores a cleaning liquid via a cleaning liquid pipe line 51. The cleaning liquid is used for the cleaning processing. A cleaning liquid pump 52 is provided in the cleaning liquid pipe line 51. The cleaning liquid pump 52 is connected to the control portion 5, and the operation of the cleaning liquid pump 52 is controlled by the control portion 5. By operating the cleaning liquid pump 52, the cleaning liquid in the cleaning liquid tank 50 is transferred into the treatment tank 2.

The medicinal solution nozzle 12 is an opening portion that communicates with the medicinal solution tank 20 via a medicinal solution pipe line 26. The medicinal solution tank 20 stores the medicinal solution. The type of the medicinal solution stored in the medicinal solution tank 20 is not particularly limited, but in the present embodiment, as an example, the medicinal solution is a disinfecting liquid used for the disinfection processing or a sterilizing liquid used for the sterilization processing. An example of the disinfecting liquid or the sterilizing liquid is an aqueous peracetic acid solution.

The medicinal solution pipe line 26 is provided with a medicinal solution pump 27. By operating the medicinal solution pump 27, the medicinal solution in the medicinal solution tank 20 is transferred into the treatment tank 2 via the medicinal solution pipe line 26 and the medicinal solution nozzle 12.

In the present embodiment, as an example, the medicinal solution can be reused in a case where there is a medicinal effect even after being used for the reprocessing. Accordingly, the endoscope reprocessor 1 recovers the medicinal solution in the treatment tank 2 and returns the recovered medicinal solution into the medicinal solution tank 20. A configuration for recovering the medicinal solution in the treatment tank 2 and returning the recovered medicinal solution to the medicinal solution tank 20 will be described later.

The drainage port 11 is an opening portion provided at the lowest position in the treatment tank 2. The drainage port 11 is connected to a discharge pipe line 21. The discharge pipe line 21 communicates with the drainage port 11 and a switching valve 22. A recovery pipe line 23 and a waste pipe line 25 are connected to the switching valve 22. The switching valve 22 can be switched to a state where the discharge pipe line 21 is closed, a state of communicating the discharge pipe line 21 and the recovery pipe line 23, or a state of communicating the discharge pipe line 21 and the waste pipe line 25. The switching valve 22 is connected to the control portion 5, and the operation of the switching valve 22 is controlled by the control portion 5.

The recovery pipe line 23 communicates the medicinal solution tank 20 and the switching valve 22. Further, the waste pipe line 25 communicates the drainage equipment for receiving the liquid discharged from the endoscope reprocessor 1 and the switching valve 22. The waste pipe line 25 is provided with a discharge pump 24. The discharge pump 24 is connected to the control portion 5 and the operation of the discharge pump 24 is controlled by the control portion 5.

When the switching valve 22 is in a closed state, the liquid can be stored in the treatment tank 2. Further, when the medicinal solution is stored in the treatment tank 2, and when the switching valve 22 is in a state of communicating the discharge pipe line 21 and the recovery pipe line 23, the medicinal solution is transferred from the treatment tank 2 to the medicinal solution tank 20.

In addition, by setting the switching valve 22 in a state of communicating the discharge pipe line 21 and the waste pipe line 25, and operating the discharge pump 24, the liquid in the treatment tank 2 is sent to the drainage equipment via the waste pipe line 25.

The circulation port 13 is an opening portion provided in the vicinity of the bottom surface of the treatment tank 2. The circulation port 13 communicates with a circulation pipe line 13a. The circulation pipe line 13a is branched into two pipe lines of an endoscope circulation pipe line 30 and a treatment tank circulation pipe line 40. In addition, a three-way valve controlled by the control portion 5 may be disposed at the branch portion. In this case, the three-way valve disposed at the branch portion of the circulation pipe line 13a can be switched to a state of communicating the circulation pipe line 13a and the endoscope circulation pipe line 30 or a state of communicating the circulation pipe line 13a and the treatment tank circulation pipe line 40.

The endoscope circulation pipe line 30 communicates the circulation pipe line 13a and a channel block 32 which will be described later. The endoscope circulation pipe line 30 is provided with a fluid sending pump 33. The fluid sending pump 33 is operated to transfer the fluid in the endoscope circulation pipe line 30 toward the channel block 32.

In addition to the above-described endoscope circulation pipe line 30, an intake pipe line 34, an alcohol pipe line 38, and a sending pipe line 31 are connected to the channel block 32. The channel block 32 connects the sending pipe line 31, the endoscope circulation pipe line 30, the intake pipe line 34, and the alcohol pipe line 38 to each other. The channel block 32 is provided with a check valve that allows the flow of the fluid from the endoscope circulation pipe line 30, the intake pipe line 34, and the alcohol pipe line 38 only toward the inside of the channel block 32. In other words, the fluid does not flow from the inside of the channel block 32 toward the endoscope circulation pipe line 30, the intake pipe line 34, and the alcohol pipe line 38.

One end portion of the intake pipe line 34 is open to the atmosphere, and the other end portion is connected to the channel block 32. Note that although not illustrated in the drawing, a filter that filters the gas passing through the filter is provided at one end portion of the intake pipe line 34. An air compressor 35 is provided in the intake pipe line 34 and is operated to transfer the gas in the intake pipe line 34 toward the channel block 32.

The alcohol pipe line 38 communicates an alcohol tank 37 that stores alcohol and the channel block 32. Examples of the alcohol stored in the alcohol tank 37 include ethanol. Alcohol concentration can be appropriately selected. The alcohol pump 39 is provided in the alcohol pipe line 38 and is operated to transfer the alcohol in the alcohol tank 37 toward the channel block 32.

The fluid sending pump 33, the air compressor 35, and the alcohol pump 39 are connected to the control portion 5, and the operations are controlled by the control portion 5. When the fluid sending pump 33 is started operating in a case where the liquid is stored in the treatment tank 2, the liquid in the treatment tank 2 is fed to the sending pipe line 31 via the circulation port 13, the circulation pipe line 13a, and the endoscope circulation pipe line 30. When the operation of the air compressor 35 is started, the air is fed into the sending pipe line 31. When the operation of the alcohol pump 39 is started, the alcohol in the alcohol tank 37 is fed into the sending pipe line 31.

The sending pipe line 31 is connected to the endoscope pipe line connection portion 16. The endoscope pipe line connection portion 16 is connected to a pipe sleeve 202 provided in the endoscope 200 via an endoscope connection tube 100. The fluid sent from the channel block 32 to the sending pipe line 31 is introduced into a pipe line 201 that communicates with the pipe sleeve 202 of the endoscope 200 via the endoscope pipe line connection portion 16. In addition, the endoscope pipe line connection portion 16 may be directly connected to the pipe sleeve 202 without going through the endoscope connection tube 100.

The circulation pipe line 13a, the endoscope circulation pipe line 30, the sending pipe line 31, the channel block 32, the fluid sending pump 33, the intake pipe line 34, and the air compressor 35 configure a fluid sending portion 70 as a fluid sending mechanism for sending the fluid into the pipe line 201 of the endoscope 200.

The treatment tank circulation pipe line 40 communicates the circulation pipe line 13a and the circulation nozzle 14. The circulation nozzle 14 is an opening portion provided in the treatment tank 2. The treatment tank circulation pipe line 40 is provided with a fluid pump 41. The fluid pump 41 is connected to the control portion 5 and the operation of the fluid pump 41 is controlled by the control portion 5.

In addition, a three-way valve 42 is provided between the fluid pump 41 of the treatment tank circulation pipe line 40 and the circulation nozzle 14. The three-way valve 42 is connected to a water supply pipe line 43. The three-way valve 42 can be switched to a state of communicating the circulation nozzle 14 and the treatment tank circulation pipe line 40 or a state of communicating the circulation nozzle 14 and the water supply pipe line 43.

The water supply pipe line 43 communicates the three-way valve 42 and a water supply source connection portion 46. The water supply pipe line 43 is provided with a water introduction valve 45 for opening and closing the water supply pipe line 43 and a water filter 44 for filtering water. The water filtered by the water filter 44 is in a sterilized state. The water supply source connection portion 46 is connected to a water supply source 49, such as water supply equipment that sends water, via a hose, for example.

The three-way valve 42 and the water introduction valve 45 are connected to the control portion 5, and the operations of these valves are controlled by the control portion 5.

In a case where the liquid is stored in the treatment tank 2, when the three-way valve 42 is in a state of communicating the circulation nozzle 14 and the treatment tank circulation pipe line 40 and the operation of the fluid pump 41 is started, the liquid in the treatment tank 2 is discharged from the circulation nozzle 14 via the circulation port 13, the circulation pipe line 13a, and the tea went tank circulation pipe line 40.

Further, when the three-way valve 42 is in a state where the circulation nozzle 14 and the water supply pipe line 43 communicate with each other and the water introduction valve 45 is in an opened state, the water supplied from the water supply source 49 is discharged from the circulation nozzle 14. The water discharged from the circulation nozzle 14 is introduced into the treatment tank 2 and used as a rinsing liquid or the like for rinsing an endoscope or the like disposed in the treatment tank 2. The water supply source connection portion 46, the water supply pipe line 43, the water introduction valve 45, the circulation nozzle 14, and the three-way valve 42 configure a liquid introduction portion as a liquid introduction mechanism for introducing the rinsing liquid into the treatment tank 2.

Further, the endoscope reprocessor 1 of the present embodiment includes the sample collection device 60 that collects a sample from the liquid in the treatment tank 2. In the present embodiment, the sample collection device 60 is provided as an example in the circulation pipe line 13a.

The sample collection device 60 includes a first filter 61, a second filter 62, and a normal pipe line 63. The sample collection device 60 allows some or all of the fluid that flows through the circulation pipe line 13a to selectively pass through any one of the first filter 61, the second filter 62, and the normal pipe line 63. The first filter 61 and the second filter 62 filter the fluid that passes therethrough. The normal pipe line 63 is a simple pipe line. The sample collection device 60 is connected to the control portion 5, and the operation of the sample collection device 60 is controlled by the control portion 5.

In a case where the sample collection device 60 is in a state of allowing the fluid that flows through the circulation pipe line 13a to pass through the first filter 61 or the second filter 62, the sample is collected from the fluid that flows through the circulation pipe line 13a by the first filter 61 or the second filter 62. Meanwhile, in a case where the sample collection device 60 is in a state of allowing the fluid that flows through the circulation pipe line 13a to pass through the normal pipe line 63, the sample is not collected from the fluid that flows through the circulation pipe line 13a.

In the endoscope reprocessor 1 of the present embodiment, in a case where the liquid is stored in the treatment tank 2, the sample collection device 60 is switched to a state where the fluid passes through the first filter 61 or the second filter 62, and then, when the operation of the fluid sending pump 33 or the fluid pump 41 is started, the sample can be collected from the liquid in the treatment tank 2 by the first filter 61 or the second filter 62.

Next, in the endoscope reprocessor 1 having the above-described configuration, an endoscope reprocessing method executed by the control portion 5 will be described.

The endoscope reprocessing method includes: step I of cleaning, disinfecting, or sterilizing an inside of the pipe line 201 and an outer surface of the endoscope 200 accommodated in the treatment tank 2; step II of rinsing the outer surface with the rinsing liquid while filling the inside of the pipe line 201 with gas; and step III of collecting a first sample from the rinsing liquid in the above-described step II. Further, the endoscope reprocessing method may further include: step IV of rinsing the inside of the pipe line 201 with the rinsing liquid; and step V of collecting a second sample from the rinsing liquid in the above-described step IV.

Figure 2:
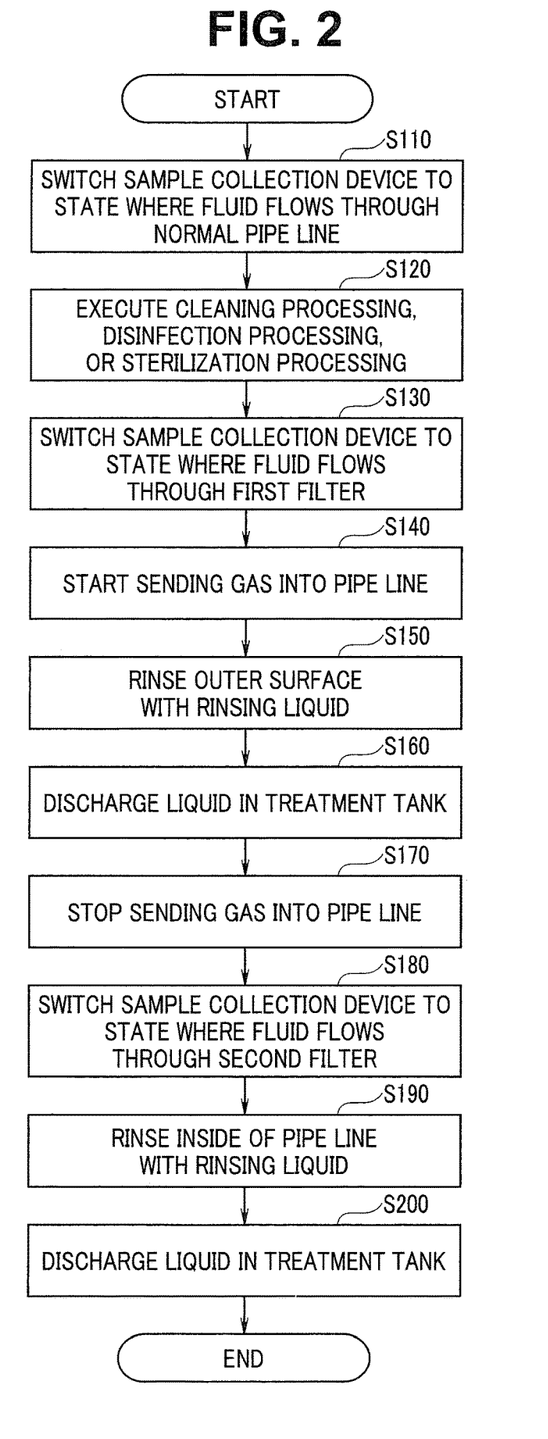
FIG. 2 is a flowchart illustrating an endoscope reprocessing method according to the first embodiment.

FIG. 2 is a flowchart of the endoscope reprocessing method. At the start of an endoscope reprocessing operation, the endoscope 200 is disposed in the treatment tank 2, and the pipe line 201 of the endoscope 200 is connected to the endoscope pipe line connection portion 16.

In the endoscope reprocessing method, first, in step S110, the control portion 5 switches the sample collection device 60 to a state where the fluid flows through the normal pipe line 63. By executing step S110, some or all of the fluid that flows through the circulation pipe line 13a flows in the normal pipe line 63.

Next, in step S120, the control portion 5 executes the cleaning processing, the disinfection processing, or the sterilization processing on the inside and the outer surface of the pipe line 201 of the endoscope 200 accommodated in the treatment tank 2. In other words, step S120 corresponds to step 1. In addition, the control portion 5 discharges the liquid from the treatment tank 2 when step S120 is completed.

Since the control by the control portion 5 in the cleaning processing, the disinfection processing, or the sterilization processing by the endoscope reprocessor 1 is known, a detailed description of the processing will be omitted.

Schematically, for example, in a case of executing the cleaning processing, the control portion 5 discharges the liquid from the treatment tank 2, and then sets the switching valve 22 to a closed state to introduce a predetermined amount of cleaning liquid and water into the treatment tank 2. Thereafter, the control portion 5 alternately executes the operations of the fluid sending pump 33 and the fluid pump 41. By this control, the cleaning liquid flows along the inside and the outer surface of the pipe line 201 of the endoscope, and the cleaning processing is performed on the inside and the outer surface of the pipe line 201.

Further, for example, in a case of executing the disinfection processing or the sterilization processing, the liquid is discharged from the inside of the treatment tank 2, and then the switching valve 22 is set to a closed state to introduce a predetermined amount of medicinal solution into the treatment tank 2. Thereafter, the control portion 5 alternately executes the operations of the fluid sending pump 33 and the fluid pump 41. By this control, the medicinal solution flows along the inside and the outer surface of the pipe line 201 of the endoscope, and the disinfection processing or the sterilization processing is performed on the inside and the outer surface of the pipe line 201.

The liquid used for executing step S120 passes through the normal pipe line 63 of the sample collection device 60.

Next, in step S130, the control portion 5 switches the sample collection device 60 to a state where the fluid flows through the first filter 61. By executing step S130, some or all of the fluid that flows through the circulation pipe line 13a passes through the first filter 61.

Next, in step S140, the control portion 5 starts operation of the air compressor 35 and starts sending gas into the pipe line 201 of the endoscope 200. By executing step S140, the inside of the pipe line 201 of the endoscope 200 is filled with gas. In the present embodiment, the gas sent into the pipe line 201 is air.

Next, in step S150, the control portion 5 rinses the outer surface of the endoscope 200 with the rinsing liquid. Specifically, in step S150, the control portion 5 first sets the switching valve 22 in a closed state, and then in a state where the three-way valve 42 communicates the circulation nozzle 14 and the water supply pipe line 43, by controlling the water introduction valve 45, the rinsing liquid is introduced to a predetermined first water level L1 in the treatment tank 2. In the present embodiment, the rinsing liquid is water supplied from the water supply source 49. The first water level L1 is a height at which the entire endoscope 200 accommodated in the treatment tank 2 is immersed in the rinsing liquid.

Note that, in the present embodiment, the rinsing liquid is water as an example, but a stripping solution may be used as a rinsing liquid. As the stripping solution, a surfactant is preferable, and a surfactant with low foaming properties is more preferable. Examples of the surfactant with low foaming properties include octylphenol ethoxylate. As octylphenol ethoxylate, for example, commercially available TRITON (registered trademark), NONIDET (registered trademark), Nikkol OP (registered trademark), Igepal CA (registered trademark), and the like may be used. Moreover, as a stripping solution that promotes the stripping of protein, a sodium dodecyl sulfate aqueous solution (SDS aqueous solution) or the like is preferable.

Although not illustrated, in a case where a stripping solution is used as the rinsing liquid, the endoscope reprocessor 1 preferably includes a stripping solution tank for storing the stripping solution and a pump for supplying the stripping solution from the stripping solution tank to the treatment tank 2.

Next, the control portion 5 operates the fluid pump 41 for a predetermined time period in a state where the three-way valve 42 communicates the circulation nozzle 14 and the treatment tank circulation pipe line 40. Accordingly, the rinsing liquid stored in the treatment tank 2 flows so as to return to the inside of the treatment tank 2 via the circulation port 13, the circulation pipe line 13a, the treatment tank circulation pipe line 40, and the circulation nozzle 14.

Due to the flow of the rinsing liquid in step S150, the outer surface of the endoscope 200 is rinsed with the rinsing liquid. In step S150, gas is sent into the pipe line 201 of the endoscope 200, the inside of the pipe line 201 is filled with air, and thus the rinsing liquid does not enter the pipe line 201. Therefore, in step S150, the inside of the pipe line 201 is not rinsed with the rinsing liquid, and only the outer surface of the endoscope 200 is rinsed with the rinsing liquid. Step S150 corresponds to step II of rinsing the outer surface of the endoscope 200 with the rinsing liquid while filling the inside of the pipe line 201 of the endoscope 200 with gas.

In step S150, some or all of the rinsing liquid passes through the first filter 61 of the sample collection device 60. In other words, in step S150, the rinsing liquid for rinsing the outer surface of the endoscope 200 is filtered by the first filter 61. Therefore, the first sample is collected by the first filter 61 from the rinsing liquid by executing step S150. Step S150 corresponds to step III of recovering the first sample from the rinsing liquid in step II.

Next, in step S160, the control portion 5 sets the switching valve 22 in a state of communicating the discharge pipe line 21 and the waste pipe line 25, and discharges the rinsing liquid in the treatment tank 2 by operating the discharge pump 24. Step S150 and step S160 may be repeatedly performed a predetermined number of times. In a case where step S150 and step S160 are performed a plurality of times, there may be an aspect of including the number of times of using the stripping solution as the rinsing liquid and the number of times of using only water as the rinsing liquid.

Next, in step S170, the control portion 5 stops the operation of the air compressor 35 and stops sending gas into the pipe line 201 of the endoscope 200.

Next, in step S180, the control portion 5 switches the sample collection device 60 to a state where the fluid flows through the second filter 62. By executing step S180, some or all of the fluid that flows through the circulation pipe line 13a passes through the second filter 62.

Next, in step S190, the control portion 5 rinses the inside of the pipe line 201 of the endoscope 200 with the rinsing liquid. Specifically, in step S190, the control portion 5 first sets the switching valve 22 in a closed state, and then in a state where the three-way valve 42 communicates the circulation nozzle 14 and the water supply pipe line 43, and by controlling the water introduction valve 45, the rinsing liquid is introduced to a predetermined second water level L2 in the treatment tank 2. In the present embodiment, the rinsing liquid is water supplied from the water supply source 49.

The second water level L2 is a height lower than the endoscope 200 accommodated in the treatment tank 2. In other words, in a state where the rinsing liquid is stored up to the second water level L2 in the treatment tank 2, the entire endoscope 200 is exposed to the air.

Next, the control portion 5 operates the fluid sending pump 33 for a predetermined time period. Accordingly, the rinsing liquid stored in the treatment tank 2 flows so as to return to the inside of the treatment tank 2 via the circulation port 13, the circulation pipe line 13a, the endoscope circulation pipe line 30, the sending pipe line 31, and the pipe line 201.

Due to the flow of the rinsing liquid in step S190, the inside of the pipe line 201 of the endoscope 200 is rinsed with the rinsing liquid. In step S190, since the outer surface of the endoscope 200 is exposed to the air, the rinsing liquid is not in contact with the outer surface. Therefore, in step S190, the outer surface of the endoscope 200 is not rinsed with the rinsing liquid, and only the inside of the pipe line 201 of the endoscope 200 is rinsed with the rinsing liquid. Step S190 corresponds to step IV of rinsing the inside of the pipe line 201 of the endoscope 200 with the rinsing liquid.

In step S190, some or all of the rinsing liquid passes through the second filter 62 of the sample collection device 60. In other words, in step S190, the rinsing liquid for rinsing the inside of the pipe line 201 of the endoscope 200 is filtered by the second filter 62. Therefore, the second sample is collected by the second filter 62 from the rinsing liquid by executing step S190. Step S190 corresponds to step V in which the second sample is recovered from the rinsing liquid in the above-described step IV.

Next, in step S200, the control portion 5 sets the switching valve 22 in a state of communicating the discharge pipe line 21 and the waste pipe line 25, and discharges the rinsing liquid in the treatment tank 2 by operating the discharge pump 24. Step S190 and step S200 may be repeatedly performed a predetermined number of times. With the above, the endoscope reprocessing method executed by the control portion 5 is completed in the endoscope reprocessor 1.

As described above, in the endoscope reprocessing method executed by the endoscope reprocessor 1 of the present embodiment, the rinsing liquid used for rinsing only the outer surface of the endoscope 200 passes through the first filter 61 in a state where the inside of the pipe line 201 is filled with air, and further, the rinsing liquid used for rinsing only the inside of the pipe line 201 passes through the second filter 62 in a state where the outer surface of the endoscope 200 is exposed to the air.

Therefore, in the endoscope reprocessing method of the present embodiment, it is possible to clearly distinguish a case where the first sample collected by the first filter 61 is attached to the outer surface of the endoscope 200 and a case where the second sample collected by the second filter 62 is attached to the inside of the pipe line 201 of the endoscope 200.

Therefore, according to the endoscope reprocessing method and the endoscope reprocessor 1 of the present embodiment, by performing detection of bacteria, proteins, and the like from the first sample and second sample, it is possible to distinguish the evaluation whether or not the reprocessing is appropriately performed with respect to the outer surface and the inside of the pipe line 201 on the endoscope 200.

Note that in the present embodiment, during the execution of the rinsing processing in step S150, the gas is continuously sent into the pipe line 201, but when the inside of the pipe line 201 is filled with air before the execution of step S150, the air may not be continuously sent during the execution of step S150. This is because, since the opening of the pipe line 201 of the actual endoscope 200 is small, the amount of rinsing liquid in the treatment tank 2 that enters the pipe line 201 is extremely small without continuously sending the gas during the execution of step S150. Further, even when the rinsing liquid enters the pipe line 201 during the execution of step S150, there is no flow of fluid for pushing the rinsing liquid out of the pipe line 201, and thus, there is no case where the liquid in the pipe line 201 comes out of the treatment tank 2 and passes through the first filter 61.

Figure 3:
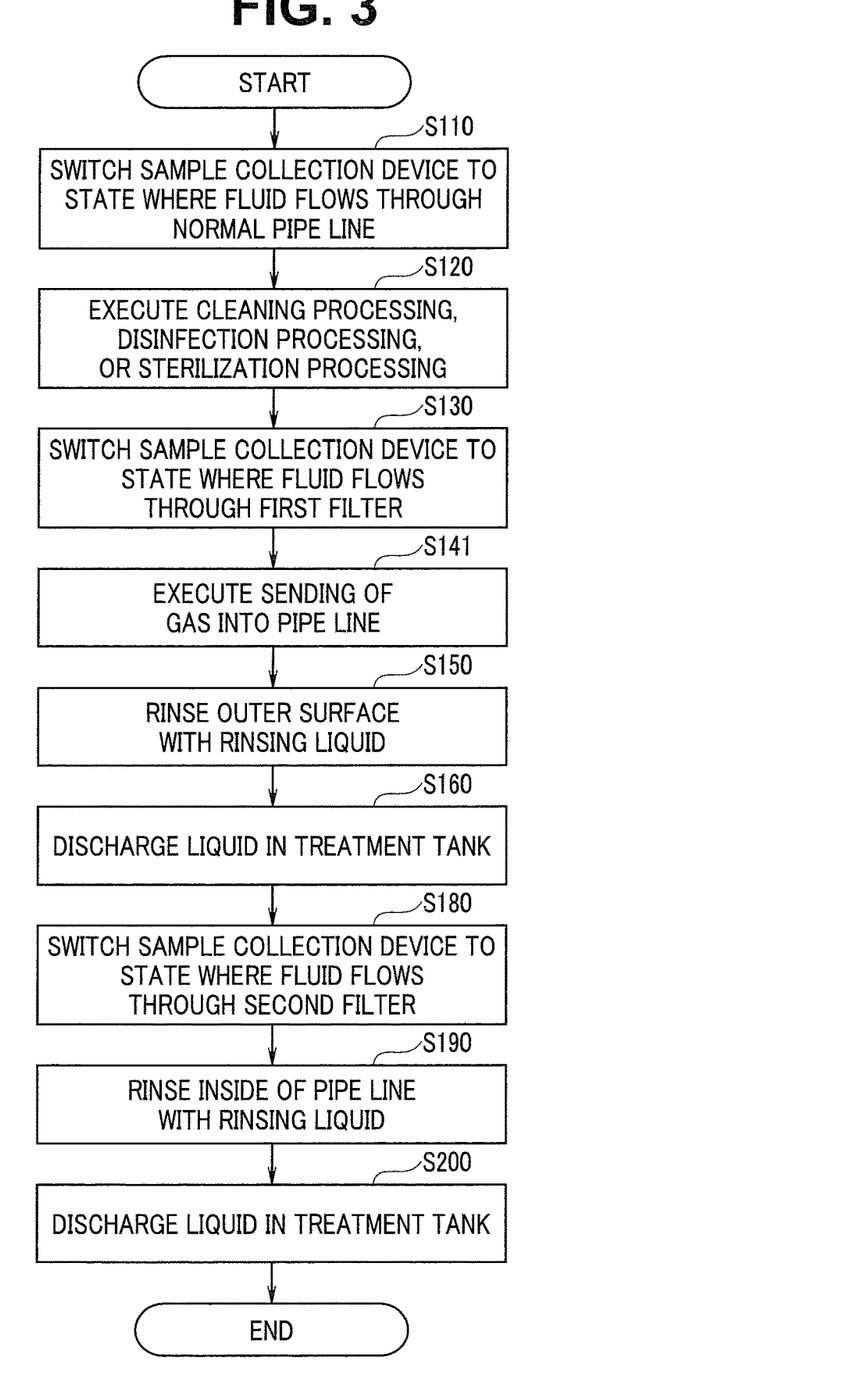
FIG. 3 is a flowchart illustrating a modification of the endoscope reprocessing method according to the first embodiment.

Therefore, as illustrated in FIG. 3 as a modification of the present embodiment, even in a case of the endoscope reprocessing method in which the gas is not sent into the pipe line 201 during the execution of the rinsing processing of step S150 and step S141 of filling the inside of the pipe line 201 with gas by sending the gas into the pipe line 201 for a predetermined time period is executed before execution of step S150, the similar effects as the effects of the above-described embodiment can be obtained.

Second Embodiment

Hereinafter, a second embodiment of the present invention will be described. Hereinafter, only differences from the first embodiment will be described, and the same components as the components in the first embodiment will be given the same reference numerals, and the description of the components will be appropriately omitted.

Figure 4:
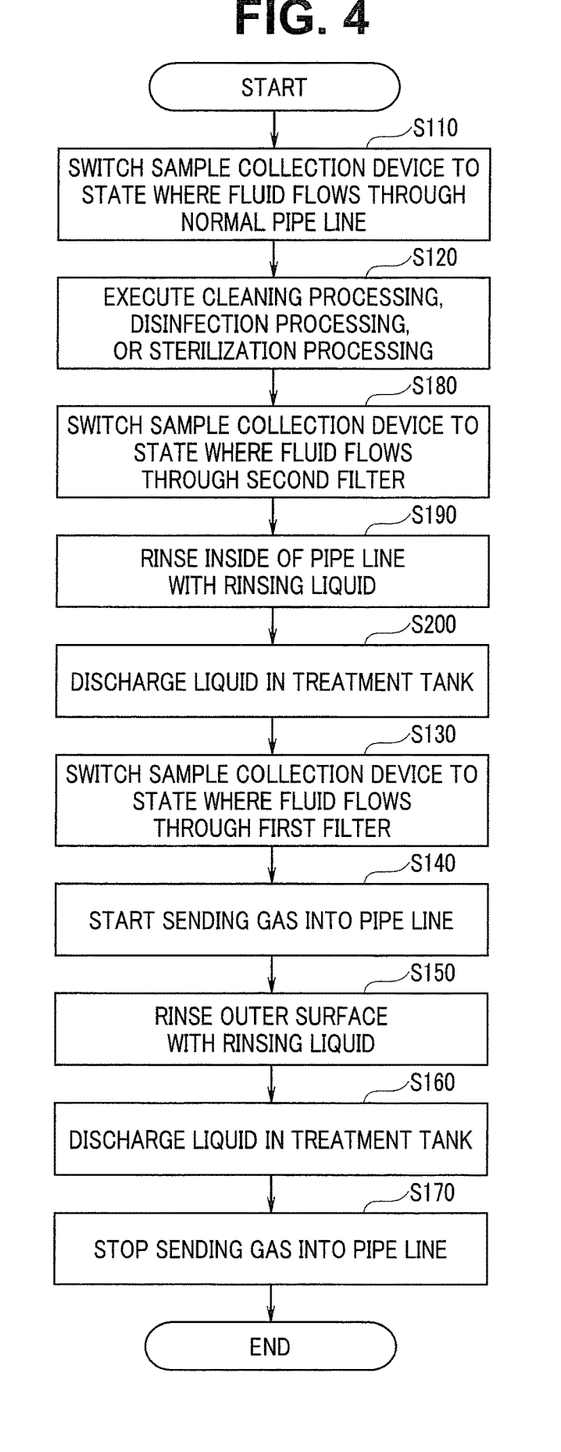
FIG. 4 is a flowchart illustrating an endoscope reprocessing method according to a second embodiment.

In the first embodiment, the second sample is collected after the first sample is collected, but this order may be reversed. In the present invention, the numbers associated with the steps do not indicate the order of the steps. In the present embodiment, after the second sample is collected, the first sample is collected. FIG. 4 illustrates a flowchart of the endoscope reprocessing method of the present embodiment.

As illustrated in FIG. 4, in the present embodiment, the control portion 5 executes an operation of allowing the rinsing liquid used for rinsing only the inside of the pipe line 201 to pass through the second filter 62 in a state where the outer surface of the endoscope 200 is exposed to the air in step S180 to step S200, and then executes an operation of allowing the rinsing liquid used for rinsing only the outer surface of the endoscope 200 to pass through the first filter 61 in a state where the inside of the pipe line 201 is filled with air in step S130 to S170.

In the endoscope reprocessing method and the endoscope reprocessor 1 of the present embodiment, it is possible to clearly distinguish a case where the first sample collected by the first filter 61 is attached to the outer surface of the endoscope 200 and a case where the second sample collected by the second filter 62 is attached to the inside of the pipe line 201 of the endoscope 200.

Therefore, according to the endoscope reprocessing method and the endoscope reprocessor 1 of the present embodiment, similar to the first embodiment, by performing detection of bacteria, proteins, and the like from the first sample and second sample, it is possible to distinguish the evaluation whether or not the reprocessing is appropriately performed with respect to the outer surface and the inside of the pipe line 201 on the endoscope 200.

In the present embodiment, as in the modification of the first embodiment described with reference to FIG. 3, the gas is not sent into the pipe line 201 during the execution of the rinsing processing of step S150, step S141 of sending the gas into the pipe line 201 for a predetermined time period and filling the inside of the pipe line 201 with gas may be executed before the execution of step S150.

Third Embodiment

Hereinafter, a third embodiment of the present invention will be described. Hereinafter, only differences from the first embodiment will be described, and the same components as the components in the first embodiment will be given the same reference numerals, and the description of the components will be appropriately omitted.

Figure 5:
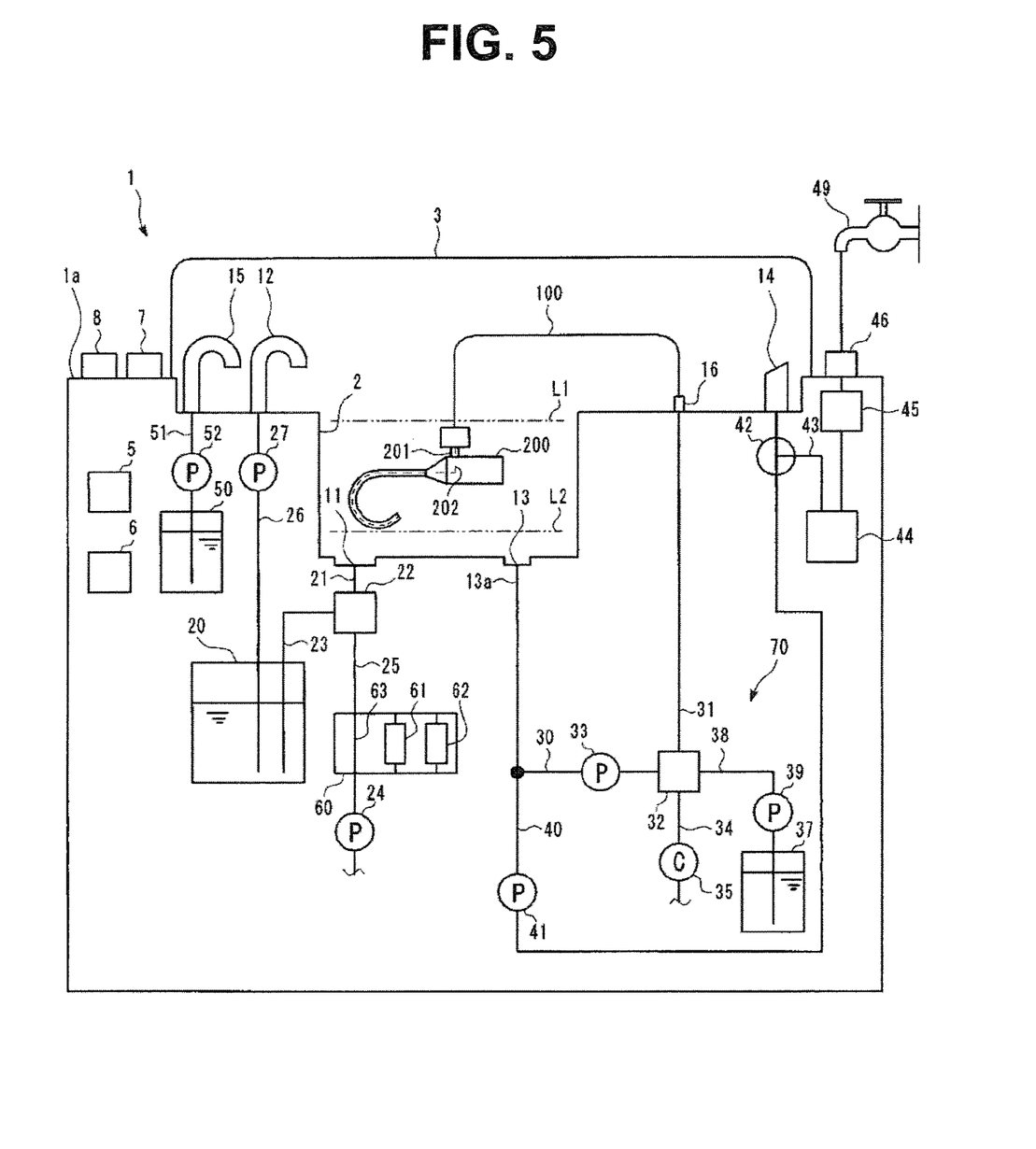
FIG. 5 is a view illustrating a configuration of an endoscope reprocessor according to a third embodiment.

FIG. 5 illustrates a configuration of the endoscope reprocessor 1 of the present embodiment. The endoscope reprocessor 1 of the present embodiment is different from that of the first embodiment in that the sample collection device 60 is placed in the waste pipe line 25.

The sample collection device 60 of the present invention allows some or all of the fluid that flows through the waste pipe line 25 to selectively pass through any one of the first filter 61, the second filter 62, and the normal pipe line 63.

In the endoscope reprocessor 1 of the present embodiment, in a case where the liquid is stored in the treatment tank 2, the sample collection device 60 is switched to a state where the fluid passes through the first filter 61 or the second filter 62, and then, sets a state where the switching valve 22 communicates with the discharge pipe line 21 and the waste pipe line 25, the sample can be collected from the liquid in the treatment tank 2 by the first filter 61 or the second filter 62 by operating the discharge pump 24.

In the present embodiment, the endoscope reprocessing method executed by the control portion 5 is the same as that in the first embodiment, but the timing when the first sample and the second sample are collected is different from the timing of the first embodiment.

In other words, in the present embodiment, in step S160 in which the rinsing liquid used for rinsing only the outer surface of the endoscope 200 in a state where the inside of the pipe line 201 is filled with air is discharged from the treatment tank 2, the first sample is collected from the rinsing liquid by the first filter 61. Further, in the present embodiment, in step S200 in which the rinsing liquid used for rinsing only the inside of the pipe line 201 in a state where the outer surface of the endoscope 200 is exposed to the air is discharged from the treatment tank 2, the first sample is collected from the rinsing liquid by the first filter 61.

In the present embodiment, step S160 corresponds to step III of recovering the first sample from the rinsing liquid in step II, and step S200 corresponds to step V of recovering the first sample from the rinsing liquid in step IV.

In the endoscope reprocessing method and the endoscope reprocessor 1 of the present embodiment, it is possible to clearly distinguish a case where the first sample collected by the first filter 61 is attached to the outer surface of the endoscope 200 and a case where the second sample collected by the second filter 62 is attached to the inside of the pipe line 201 of the endoscope 200.

Therefore, according to the endoscope reprocessing method and the endoscope reprocessor 1 of the present embodiment, similar to the first embodiment, by performing detection of bacteria, proteins, and the like from the first sample and second sample, it is possible to distinguish the evaluation whether or not the reprocessing is appropriately performed with respect to the outer surface and the inside of the pipe line 201 on the endoscope 200.

Note that, in the present embodiment, similar to the modification of the first embodiment described with reference to FIG. 3, the gas is not sent into the pipe line 201 during the execution of the rinsing processing of step S150, step S141 of sending the gas into the pipe line 201 for a predetermined time period and filling the inside of the pipe line 201 with gas may be executed before the execution of step S150.

In the present embodiment, similar to the second embodiment, the first sample may be collected after the second sample is collected.

Fourth Embodiment

Hereinafter, a fourth embodiment of the present invention will be described. Hereinafter, only differences from the first embodiment will be described, and the same components as the components in the first embodiment will be given the same reference numerals, and the description of the same components will be appropriately omitted.

Figure 6:
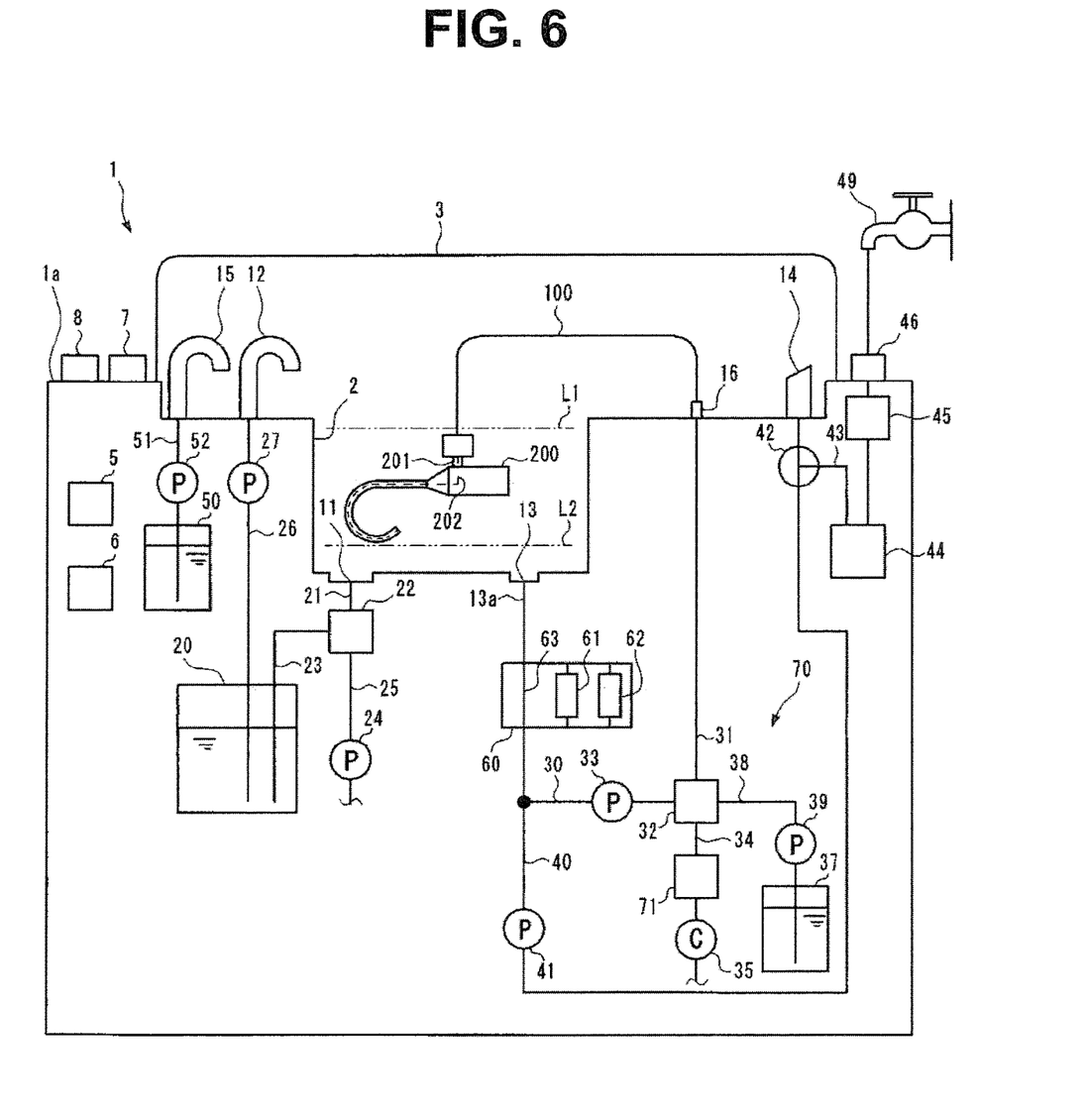
FIG. 6 is a view illustrating a configuration of an endoscope reprocessor according to a fourth embodiment.

FIG. 6 illustrates a configuration of the endoscope reprocessor 1 of the present embodiment. The endoscope reprocessor 1 according to the present embodiment is different from the first embodiment in that the fluid sending portion 70 includes an adjustment portion 71.

The adjustment portion 71 as an adjustment mechanism adjusts the pressure or flow rate of the gas that is sent from the fluid sending portion 70 and sent into the pipe line 201 of the endoscope 200. In the present embodiment, as an example, the adjustment portion 71 is provided in a section between the channel block 32 of the intake pipe line 34 and the air compressor 35.

In the present embodiment, the adjustment portion 71 is a regulator capable of switching the presence or absence of operation based on the control of the control portion 5. In a case where the pressure of the gas sent from the air compressor 35 is a first pressure P1, the adjustment portion 71 reduces a pressure of the gas sent from the fluid sending portion 70 in the operation to a second pressure P2 lower than the first pressure P1. In a case where the adjustment portion 71 is not operating, the pressure of the gas sent from the fluid sending portion 70 is the first pressure P1.

In other words, in a case where the gas is sent from the fluid sending portion 70 into the pipe line 201, the flow velocity of the gas in the pipe line 201 is lower when the adjustment portion 71 is operating than that when the adjustment portion 71 is not operating.

Since the first pressure P1 is a value necessary for allowing the liquid in the pipe line 201 to flow into the treatment tank 2, when the gas is sent into the pipe line 201 at the first pressure P1 in step S140, a possibility that bacteria attached to the inside of the pipe line 201 flows out into the treatment tank 2 is considered. Here, in the present embodiment, when filling the inside of the pipe line 201 with gas in step S140, the pressure of the gas sent into the pipe line 201 is reduced to reduce the flow velocity of the gas in the pipe line 201, it is possible to reduce the possibility that bacteria attached to the inside of the pipe line 201 flows into the treatment tank 2.

Note that in addition, the value of the second pressure P2 may be variable. The second pressure P2 is preferably such that the flow velocity of the gas in the pipe line 201 during the operation is less than 2 m/s.

According to the endoscope reprocessor 1 of the present embodiment, it is possible to more clearly distinguish the evaluation whether or not the reprocessing is appropriately performed with respect to the outer surface and the inside of the pipe line 201 on the endoscope 200.

Note that in the present embodiment, similar to the modification of the first embodiment described with reference to FIG. 3, the gas is not sent into the pipe line 201 during the execution of the rinsing processing of step S150, step S141 of sending the gas into the pipe line 201 for a predetermined time period and filling the inside of the pipe line 201 with gas may be executed before the execution of step S150.

In the present embodiment, similar to the second embodiment, the first sample may be collected after the second sample is collected.

Further, similar to the third embodiment, the endoscope reprocessor 1 of the present embodiment may include the sample collection device 60 in the waste pipe line 25.

Figure 7:
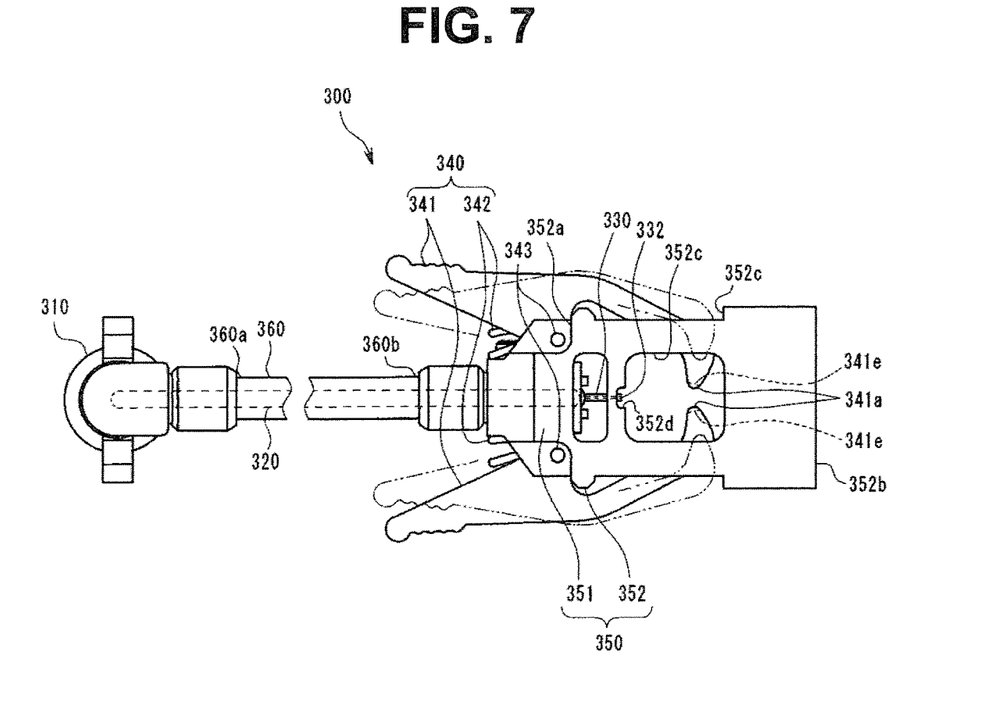
FIG. 7 is a view illustrating a configuration of a connection tool.
Figure 8:
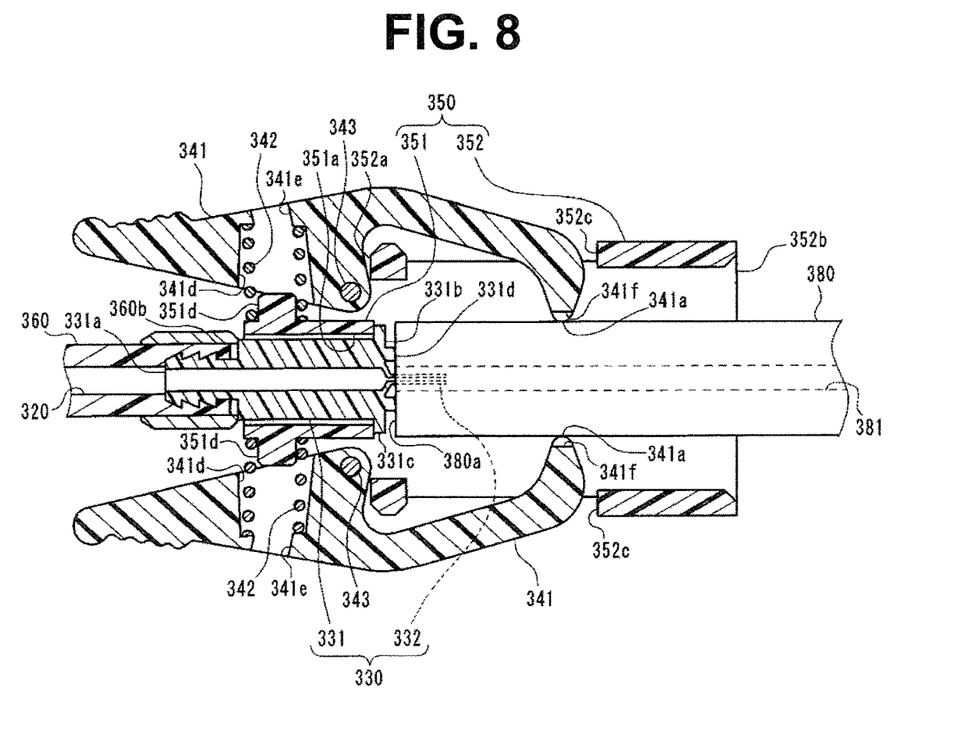
FIG. 8 is a partial sectional view of the connection tool.

FIG. 7 illustrates a connection tool 300. FIG. 8 illustrates a partial sectional view of the connection tool 300. The connection tool 300 is a device for introducing the fluid into a pipe line 381 of a tubular medical device 380 (illustrated in FIG. 8). The connection tool 300 is used together with a reprocessor that performs the reprocessing on the medical device 380. The tubular medical device 380 is a dilator as an example. In addition, the tubular medical device 380 may be an endoscope having the pipe line 381.

The connection tool 300 includes a connection portion 310, a tube 360, a nozzle 330, a flow path 320, a cover portion 350, and a grasping portion 340. FIG. 8 is a sectional view of the nozzle 330, the cover portion 350, and the grasping portion 340.

The connection portion 310 is a part connected to a connector provided in the reprocessor. A base end 360a of the tube 360 is coupled to the connection portion 310. The connector of the reprocessor discharges the fluid when the reprocessing is executed. The connection portion 310 communicates the connector and the inside of the tube 360 by being connected to the connector.

As illustrated in FIG. 8, a tip end 360b of the tube 360 is coupled to the nozzle 330. The nozzle 330 includes a cylindrical portion 331 and a narrow tube portion 332. A base end 331a of the cylindrical portion 331 is coupled to the tip end 360b of the tube 360. A tip end 331b of the cylindrical portion 331 is provided with the narrow tube portion 332.

The narrow tube portion 332 protrudes from the tip end 331b of the cylindrical portion 331. An outer diameter of the narrow tube portion 332 is smaller than an outer diameter of the cylindrical portion 331. Further, the outer diameter of the narrow tube portion 332 is smaller than the inner diameter of the pipe line 381 provided in the medical device 380. The inside of the narrow tube portion 332 communicates with the inside of the tube 360. In other words, the connection tool 300 includes the flow path 320 having a base end provided at the connection portion 310 and a tip end provided at the narrow tube portion 332.

The base end of the flow path 320 communicates with the connector by connecting the connection portion 310 to the connector of the reprocessor. Further, the tip end of the flow path 320 is opened at a tip end 332a of the narrow tube portion 332. Therefore, the fluid discharged from the connector of the reprocessor is discharged from the tip end 332a of the narrow tube portion 332 via the flow path 320.

The tip end 331b of the cylindrical portion 331 is provided with a flange portion 331c and one or a plurality of protrusions 331d. The flange portion 331c protrudes radially outward from the tip end 331b of the cylindrical portion 331. The protrusion 331d is disposed around the narrow tube portion 332 and protrudes from the tip end 331b of the cylindrical portion 331 in the same direction as the narrow tube portion 332. The narrow tube portion 332 protrudes toward the tip end side from the protrusion 331d.

The cover portion 350 includes an inner cylindrical portion 351 and an outer cylindrical portion 352. The inner cylindrical portion 351 has a through hole 351a into which the cylindrical portion 331 is inserted. An inner diameter of the through hole 351a is larger than an outer diameter of the cylindrical portion 331. In other words, there is a gap between the inner peripheral surface of the through hole 351a and the outer peripheral surface of the cylindrical portion 331. Further, the inner diameter of the through hole 351a is smaller than an outer diameter of the flange portion 331c. Therefore, the nozzle 330 is positioned with respect to the cover portion 350 when the flange portion 331c hits the inner cylindrical portion 351.

The outer cylindrical portion 352 is a cylindrical part fixed to the inner cylindrical portion 351. The outer cylindrical portion 352 is connected to the inner cylindrical portion 351 at a base end 352a. A tip end 352b of the outer cylindrical portion 352 is open. The outer cylindrical portion 352 surrounds the narrow tube portion 332 and is disposed substantially parallel to the narrow tube portion 332. Further, the tip end 352b of the outer cylindrical portion 352 protrudes from the tip end 332a of the narrow tube portion 332.

In a case where the outer cylindrical portion 352 is viewed from the tip end 352b side, the tip end 331b of the cylindrical portion 331 is exposed on the bottom surface portion of the outer cylindrical portion 352. In other words, the narrow tube portion 332 and the protrusion 331d are disposed on the bottom surface portion of the outer cylindrical portion 352.

A plurality of through holes 352c are formed on the side surface of the outer cylindrical portion 352. The user can see the inside of the outer cylindrical portion 352 from the outside of the outer cylindrical portion 352 through the through hole 352c. Further, a notch 352d is formed at a periphery portion of some of the through holes 352c.

A pair of notches 352d is formed in the outer cylindrical portion 352. The pair of notches 352d are arranged at line-symmetric positions with the central axis of the outer cylindrical portion 352 as the symmetry axis. In a case where the nozzle 330 (narrow tube portion 332) is straight and has a normal shape, the tip end of the narrow tube portion 332 is positioned between the pair of notches 352d. Therefore, in a case where the outer cylindrical portion 352 is viewed from the outside of the side surface, when the narrow tube portion 332 is straight, the tip end of the narrow tube portion 332 can be seen through the notch 352d. Accordingly, the user can determine whether or not the narrow tube portion 332 is straight or bent depending on whether or not the tip end of the narrow tube portion 332 can be seen from the notch 352d.

As illustrated in FIG. 8, the medical device 380 can be inserted into the outer cylindrical portion 352 from the opening of the tip end 352b of the outer cylindrical portion 352. The tip end 380a of the medical device 380 inserted into the outer cylindrical portion 352 faces the tip end 331b of the cylindrical portion 331 of the nozzle 330. At this time, the narrow tube portion 332 is inserted into the pipe line 381 of the medical device 380. When the tip end 380a of the medical device 380 hits the protrusion 331d, the medical device 380 is positioned in the long axis direction with respect to the narrow tube portion 332. In addition, when the tip end 380a of the medical device 380 hits the protrusion 331d, the adhesion of the tip end 380a of the medical device 380 and the tip end 331b of the cylindrical portion 331 is prevented, and a gap is generated between these tip ends.

The grasping portion 340 grasps the medical device 380 inserted into the outer cylindrical portion 352 from the side. The grasping portion 340 has a clothes pin-like configuration. The grasping portion 340 includes a pair of arm portions 341 and a pair of springs 342.

The pair of arm portions 341 can swing around a rotation shaft 343 with respect to the cover portion 350. The tip ends 341a of the pair of arm portions 341 extend from the outside of the outer cylindrical portion 352 to the inside of the outer cylindrical portion 352 via the through hole 352c. The tip ends 341a of the pair of arm portions 341 face each other inside the outer cylindrical portion 352. As the pair of arm portions 341 swings around the rotation shaft 343, the distance between the tip ends 341a of the pair of arm portions 341 changes. The rotation shaft 343 is disposed in the vicinity of the base end 352a of the outer cylindrical portion 352 of the cover portion 350.

The pair of springs 342 urges the pair of arm portions 341 in the direction in which the tip ends 341a approach each other. The spring 342 is a compression coil spring.

A cylindrical protrusion 351d is formed to protrude radially outward from the outer peripheral surface of the inner cylindrical portion 351. An outer diameter of the protrusion 351d is smaller than an inner diameter of the spring 342. In addition, a bottomed hole 341d is formed at a location that faces the protrusion 351d of the arm portion 341. The hole 341d has a shape into which the spring 342 can be inserted. The protrusion 351d and the hole 341d are disposed at a location farther from the tip end 341a of the arm portion 341 than the rotation shaft 343. By inserting the protrusion 351d into one end of the spring 342 and inserting the other end of the spring 342 into the hole 341d, the spring 342 is held between the inner cylindrical portion 351 and the arm portion 341.

A through hole 341e that penetrates the arm portion 341 is formed on the bottom surface of the hole 341d. The inner diameter of the through hole 341e is smaller than the outer diameter of the spring 342. When the reprocessing is executed, the fluid flows through the through hole 341e, and thus, the fluid flows in the hole 341d and around the spring 342.

As illustrated in FIG. 8, the medical device 380 is held by tip ends 341a of the pair of atm portions 341, the medical device 380 is held in the outer cylindrical portion 352. As described above, in this state, the narrow tube portion 332 is inserted into the pipe line 381 of the medical device 380.

At tip ends 341a of each of the pair of arm portions 341, notches 341f are formed. The notch 341f is a groove carved in a direction along the long axis of the medical device 380. The notch 341f is provided at the center of the arm portion 341 in the thickness direction. Therefore, the grasping portion 340 can stably hold the medical device 380 at the center in the outer cylindrical portion 352.

As described above, the connection tool 300 has a structure in which the medical device 380 is grasped by the grasping portion 340 in a state where the narrow tube portion 332 that discharges the fluid is inserted into the pipe line 381 of the medical device 380. The connection tool 300 can hold the narrow tube portion 332 in the pipe line 381 without coming into contact with the inner wall surface of the pipe line 381. Therefore, the connection tool 300 can bring the part of the inner wall surface of the pipe line 381 that faces the narrow tube portion 332 into contact with the fluid, such as a medicinal solution, while holding the medical device 380 by the grasping portion 340.

The present invention is not limited to the above-described embodiments, and can be appropriately changed without departing from the spirit or idea of the invention that can be read from the claims and the entire specification, and an endoscope reprocessing method and the endoscope reprocessor according to the modification are also included in the technical scope of the present invention.

What is claimed is:

1. An endoscope reprocessing method comprising:
   cleaning, disinfecting, or sterilizing an inside of a pipe line and an outer surface of an endoscope accommodated in a treatment tank;
   at a first time subsequent to the cleaning, rinsing the outer surface of the endoscope with a first portion of rinsing liquid;
   concurrently with the rinsing of the outer surface, filling the inside of the pipe line of the endoscope with gas;
   subsequent to or concurrent with the rinsing of the outer surface, collecting a first sample from the first portion of the rinsing liquid used for rinsing the outer surface of the endoscope;
   at a second time different from the first time, rinsing the inside of the pipe line of the endoscope with a second portion of rinsing liquid; and
   subsequent to or concurrent with the rinsing of the inside of the pipe line, collecting a second sample from the second portion of the rinsing liquid used for rinsing the inside of the pipe line of the endoscope.

2. The endoscope reprocessing method according to claim 1, wherein air is continuously fed into the pipe line while the outer surface of the endoscope is rinsed with the first portion of the rinsing liquid.

3. The endoscope reprocessing method according to claim 2, wherein a flow velocity of the gas in the pipe line while the outer surface of the endoscope is rinsed with the first portion of the rinsing liquid is less than 2 m/s.

4. The endoscope reprocessing method according to claim 1, wherein the outer surface of the endoscope is in a state of being exposed to air while the inside of the pipe line of the endoscope is rinsed with the second portion of the rinsing liquid.

5. The endoscope reprocessing method according to claim 1, wherein the first portion of the rinsing liquid is different from the second portion of the rinsing liquid.

6. The endoscope reprocessing method according to claim 5, wherein the rinsing of the inside of the pipe line of the endoscope is performed after the rinsing of the outer surface of the endoscope.

7. The endoscope reprocessor according to claim 6, wherein the rinsing of the inside of the pipe line of the endoscope is performed after the rinsing of the outer surface of the endoscope.

8. The endoscope reprocessor according to claim 6, wherein the rinsing of the outer surface of the endoscope is performed after the rinsing of the inside of the pipe line of the endoscope.

9. The endoscope reprocessing method according to claim 5, wherein the rinsing of the outer surface of the endoscope is performed after the rinsing of the inside of the pipe line of the endoscope.

10. The endoscope reprocessing method according to claim 1, wherein the rising of the outer surface of the endoscope is performed at a different time than the rinsing of the inside of the pipe line.

11. The endoscope reprocessing method according to claim 1, wherein
    the collecting of the first sample is performed during the rinsing of the outer surface of the endoscope, and
    the collecting of the second sample is performed during the rinsing of the inside of the pipe line.

12. An endoscope reprocessor comprising:
    a treatment tank configured to accommodate an endoscope and to be able to store a liquid;
    one or more pumps configured to send a fluid into a pipe line of the endoscope accommodated in the treatment tank;
    a valve configured to introduce a rinsing liquid into the treatment tank;
    one or more filters configured to collect a sample from the liquid in the treatment tank; and
    a processor, wherein the processor is configured to:
        control the one or more pumps to clean, disinfect or sterilize an inside of the pipe line and an outer surface of the endoscope accommodated in the treatment tank,
        control the valve to introduce the rinsing liquid into the treatment tank to rinse the outer surface of the endoscope with a first portion of the rinsing liquid while concurrently sending gas from the one or more pumps to fill the inside of the pipe line of the endoscope with gas,
        control the one or more filters to collect a first sample from the first portion of the rinsing liquid used for rinsing the outer surface of the endoscope,
        control the one or more pumps to send a second portion of the rinsing liquid to rinse the inside of the pipe line of the endoscope with the second portion of the rinsing liquid, and
        control the one or more filters to collect a second sample from the second portion of the rinsing liquid used for rinsing the inside of the pipe line of the endoscope.

13. The endoscope reprocessor according to claim 12, wherein the air is continuously fed into the pipe line while the outer surface of the endoscope is rinsed with the first portion of the rinsing liquid.

14. The endoscope reprocessor according to claim 13, further comprising:
    a regulator configured to adjust a pressure or a flow rate of the gas sent from the fluid sending mechanism, wherein
    a flow velocity of the gas in the pipe line while the outer surface of the endoscope is rinsed with the first portion of the rinsing liquid is set to be less than 2 m/s by the regulator.

15. The endoscope reprocessor according to claim 12, wherein the outer surface of the endoscope is in a state of being exposed to the air while the inside of the pipe line of the endoscope is rinsed with the second portion of the rinsing liquid.

16. The endoscope reprocessor according to claim 12, wherein the first portion of the rinsing liquid is different from the second portion of the rinsing liquid.

17. The endoscope reprocessor according to claim 12, wherein the rising of the outer surface of the endoscope is performed at a different time than the rinsing of the inside of the pipe line.

18. The endoscope reprocessor according to claim 12, wherein
    the collecting of the first sample is performed during the rinsing of the outer surface of the endoscope, and
    the collecting of the second sample is performed during the rinsing of the inside of the pipe line.

* * * * *